United States Patent
Armstrong

[11] Patent Number: 6,015,968
[45] Date of Patent: Jan. 18, 2000

[54] MICROWAVE DISTILLATION APPARATUS, AND VESSEL-BIASING ASSEMBLY

[76] Inventor: Bernard Armstrong, 1716-2G Charleston Place Ln., Charlotte, N.C. 28212

[21] Appl. No.: 09/008,984

[22] Filed: Jan. 20, 1998

Related U.S. Application Data

[62] Division of application No. 08/542,463, Oct. 12, 1995, Pat. No. 5,711,857.

[51] Int. Cl.[7] .................................................. H05B 6/80
[52] U.S. Cl. .................... 219/687; 219/686; 220/316; 220/326; 422/21
[58] Field of Search ..................... 219/686, 687, 219/688, 679, 734, 735; 220/315, 316, 323, 326, 327; 202/235, 269; 422/21, 102, 103, 104

[56] References Cited

U.S. PATENT DOCUMENTS

| | | |
|---|---|---|
| 4,144,435 | 3/1979 | Clark et al. . |
| 4,313,798 | 2/1982 | Myers, Jr. .............................. 219/686 |
| 4,363,639 | 12/1982 | Gladon . |
| 4,490,597 | 12/1984 | Mengel .................................. 219/686 |
| 4,736,083 | 4/1988 | Saville .................................... 219/686 |
| 4,826,575 | 5/1989 | Karamian . |
| 4,861,556 | 8/1989 | Neas et al. . |
| 4,882,286 | 11/1989 | Neas et al. . |
| 4,946,797 | 8/1990 | Neas et al. . |
| 5,338,409 | 8/1994 | Heierli . |
| 5,407,641 | 4/1995 | Katschnig et al. ...................... 219/679 |

*Primary Examiner*—Philip H. Leung
*Attorney, Agent, or Firm*—Adams Law Firm, P.A.

[57] ABSTRACT

A microwave distillation apparatus is provided. The apparatus includes a microwave heating chamber having a plurality of walls. A vessel is located within the chamber for containing a liquid to be distilled. The vessel has a mouth for receiving the liquid. A connecting tube extends though an opening formed in one of the plurality of chamber walls. The connecting tube has a first end thereof for sealably engaging the mouth of the vessel, and a second end thereof extending outwardly from the chamber. A biasing assembly is located outside of the chamber, and engages the connecting tube with a biasing force to maintain the seal between the connecting tube and the mouth of the vessel. A distillate capture assembly is connected to the connecting tube for receiving vapors emitted from the liquid when heated, and for condensing the vapors into a liquid distillate for capture and storage.

2 Claims, 8 Drawing Sheets

1

MICROWAVE DISTILLATION APPARATUS, AND VESSEL-BIASING ASSEMBLY

This application is a division of application Ser. No. 08/542,463, filed on Oct. 12, 1995 U.S. Pat. No. 5,711,857.

TECHNICAL FIELD AND BACKGROUND OF THE INVENTION

This invention relates to a microwave distillation apparatus, and vessel-biasing assembly. The invention is applicable for quick and efficient distillation of beverages, such as citrus juices, using microwave energy. For example, a common practice in the juice industry includes extracting the juice from fresh fruit, removing a substantial portion of water from the juice to form a concentrate, shipping the concentrate to a processing and testing facility, and then returning a proper amount of water back into the concentrate before delivering the juice to a grocery store or other end user.

A number of quality assurance tests are performed during rehydration of the juice concentrate, and before the juice is bottled and sold. One key test relates to the amount of volatile juice flavorings, or chemical compounds known as essence, present in the juice after shipment. This essence is generally obtained for testing through distillation.

According to one prior art distillation process, a standard electrical-resistance heating element is used to bring a juice sample to boil. A portion of the heated sample is thereby converted to vapors which pass into a condensing coil. In the condensing coil, the juice vapors are cooled and returned to a liquid state. A collection vessel collects the distillate for essence testing. As a result of these tests, the essence level is adjusted accordingly during rehydration of the juice.

This distillation process is generally time consuming and inefficient. Since the juice sample must be refrigerated prior to testing, the necessary heating time using a conventional electrical element typically requires as much as 40 minutes.

In an effort to speed up the boiling time of the sample, the Applicant discovered the advantages of using a microwave heating unit in the distillation process. The boiling time was decreased to about 4 minutes using microwave energy.

An initial embodiment of the Applicant's invention is shown in FIGS. 1 and 2. This distillation apparatus "D" utilized a conventional microwave unit "U", and a flask "F" located within the microwave unit for containing a juice sample to be distilled. The flask "F" was positioned above the floor of the microwave unit on a pedestal spacer "P". A glass connecting tube "T" extended through a top wall opening in the microwave unit "U", and into sealing engagement with a mouth of the flask "F". During heating of the juice sample, it was essential that the seal between the connecting tube "T" and the mouth of the flask "F" be maintained in order to properly obtain the distillate, and to achieve accurate testing of the essence.

To maintain this seal, the Applicant constructed the pedestal spacer "P" as shown in FIG. 2 with telescoping elements, and a resilient metal coil spring "S" for permitting biasing movement of the top of the spacer as indicated by the direction arrow Thus, when the flask "F" was placed upon the pedestal spacer "P" within the microwave unit "U" the spring "S" urged the flask "F" upwardly to create and maintain the seal between the mouth of the flask and the connecting tube "T".

The opposite end of the connecting tube "T" extended outwardly from the microwave unit, and was fixedly secured to a housing "H" mounted on the top wall of the microwave unit "U". The connecting tube "T" was connected to a vapor transfer assembly "V" and condenser assembly "C" where vapors of the heated juice sample were cooled and transformed into a liquid distillate. The distillate was captured in a conventional graduated cylinder "G" for testing.

Although this distillation apparatus was far superior to other prior art devices using electrical heating elements, it nevertheless suffered from disadvantages and limitations. One disadvantage was the use of a metal coil spring within the microwave unit. The metal spring absorbed microwave energy otherwise usable for heating the juice sample, and ultimately lost its resiliency over a relatively short period of use. Moreover, due to the relatively heavy weight of the flask, the spring was required to provide a substantial upward force to properly maintain the seal between the connecting tube and mouth of the flask. This made it difficult and awkward to insert and remove the flask from within the microwave unit.

In view of these and other problems, the Applicant modified the distillation apparatus to locate the biasing assembly outside of the microwave heating unit. The biasing assembly of the present invention acts with a greater biasing force directly upon the connecting tube, as opposed to the flask, and provides and maintains a more secure seal between the connecting tube and mouth of the flask. The flask, connecting tube, and vapor transfer assembly of the distillation apparatus reside in substantial linear alignment. Thus, the force of the biasing assembly is transferred linearly through these elements, and acts to strengthen the respective sealing connections between these elements during the distillation process. Moreover, because the metal spring is not directly exposed to microwave energy, the time required for heating the juice sample is reduced, and the useful life of the spring is extended.

SUMMARY OF THE INVENTION

Therefore, it is an object of the invention to provide a distillation apparatus which utilizes microwave energy to quickly and efficiently heat a liquid sample to be distilled.

It is another object of the invention to provide a distillation apparatus which includes a vessel-biasing assembly located outside of the microwave heating unit for maintaining sealing engagement between a connecting tube and the mouth of a vessel.

It is another object of the invention to provide a distillation apparatus wherein the biasing assembly maintains a proper seal between the mouth of a sample-containing flask and a glass connecting tube extending outwardly from the microwave unit.

It is another object of the invention to provide a microwave distillation apparatus which includes ready means for coupling and uncoupling the mouth of the sample-containing flask and the connecting tube.

It is another object of the invention to provide a distillation apparatus which includes glass elements for containing the sample liquid, vapors, and distillate during the distillation process.

It is another object of the invention to provide a distillation apparatus which includes elements which will not degrade or leak over a relatively short period of use.

It is another object of the invention to provide a distillation apparatus which does not use energy absorbing material, such as metal, within the microwave unit during the distillation process.

These and other objects of the present invention are achieved in the preferred embodiments disclosed below by providing a microwave distillation apparatus. The apparatus includes a microwave heating chamber having a plurality of walls. Microwave generating means is provided for introducing microwave energy into the heating chamber. A vessel is located within the chamber for containing a liquid to be distilled. The vessel has a mouth for receiving the liquid. A connecting tube extends though an opening formed in one of the plurality of chamber walls. The connecting tube has a first end thereof for sealably engaging the mouth of the vessel, and a second end thereof extending outwardly from the chamber.

Biasing means is located outside of the chamber, and engages the connecting tube with a biasing force to maintain the seal between the connecting tube and the mouth of the vessel. Distillate capture means is connected to the connecting tube for receiving vapors emitted from the liquid when heated, and for condensing the vapors into a liquid distillate for capture and storage.

According to one preferred embodiment of the invention, a housing surrounds the second end of the connecting tube, and is mounted outside of the chamber adjacent to the opening formed in one of the plurality of chamber walls. The housing includes an inwardly-extending top flange and an inside shoulder spaced apart from the top flange.

According to another preferred embodiment of the invention, a cylinder assembly is provided for movement within the housing. The cylinder assembly includes a top ring engaging the connecting tube and an outwardly-extending bottom flange. The bottom flange of the cylinder assembly contacts the inside shoulder of the housing to restrict movement of the cylinder assembly within the housing in a direction towards the vessel.

According to yet another preferred embodiment of the invention, the biasing means includes a coil spring located between and engaging the inwardly-extending top flange of the housing and the outwardly-extending bottom flange of the cylinder assembly. The spring normally urges the bottom flange of the cylinder assembly against the inside shoulder of the housing to thereby maintain the seal between the connecting tube and the mouth of the vessel.

According to yet another preferred embodiment of the invention, the distillate capture means includes vapor transfer means. The vapor transfer means is connected to the second end of the connecting tube for receiving vapors emitted from the liquid contained in the vessel when heated in the chamber.

According to yet another preferred embodiment of the invention, the vapor transfer means includes a surge bulb mounted in linear registration with the connecting tube, and having an opening therein sealably connected to the second end of the connecting tube.

According to yet another preferred embodiment of the invention, an integrally formed neck is provided opposite the opening of the surge bulb for limiting the passage of heated liquid outwardly from the surge bulb.

According to yet another preferred embodiment of the invention, a deflector cylinder is integrally formed with the neck, and is located in linear registration with the surge bulb and connecting tube. The deflector cylinder includes a deflector plate for blocking the passage of heated liquid outwardly from the deflector cylinder while permitting free passage of vapors therethrough.

According to yet another preferred embodiment of the invention, a vapor transfer tube is connected to the deflector cylinder for receiving vapors to be distilled.

According to yet another preferred embodiment of the invention, the distillate capture means includes condenser means connected to the vapor transfer means for condensing the vapors into the liquid distillate.

According to yet another preferred embodiment of the invention, the condenser means includes a condenser assembly.

According to yet another preferred embodiment of the invention, the condenser assembly includes a cooling jacket for recycling a cooling fluid therein, and a condenser coil located within the cooling jacket.

According to yet another preferred embodiment of the invention, the cooling jacket includes an inlet and an outlet for receiving and dispensing the cooling fluid.

According to yet another preferred embodiment of the invention, the distillate capture means includes a collection vessel positioned adjacent to the condenser means for capturing and storing the distillate.

According to another preferred embodiment of the invention, a vessel for being located within a microwave heating chamber, and having a mouth for receiving a liquid is provided for use in combination with a connecting tube for extending through a wall of the heating chamber and into sealing engagement with the mouth of the vessel, and biasing means located outside of the heating chamber. The biasing means engages the connecting tube with a biasing force to maintain the seal between the connecting tube and the mouth of the vessel.

According to yet another preferred embodiment of the invention, a vessel-biasing assembly is provided for cooperating with a microwave heating chamber, a vessel located within the heating chamber, and a connecting tube extending through a wall of the heating chamber and into sealing engagement with a mouth of the vessel. The biasing assembly is located outside of the heating chamber, and engages the connecting tube with a biasing force to maintain the seal between the connecting tube and the mouth of the vessel.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
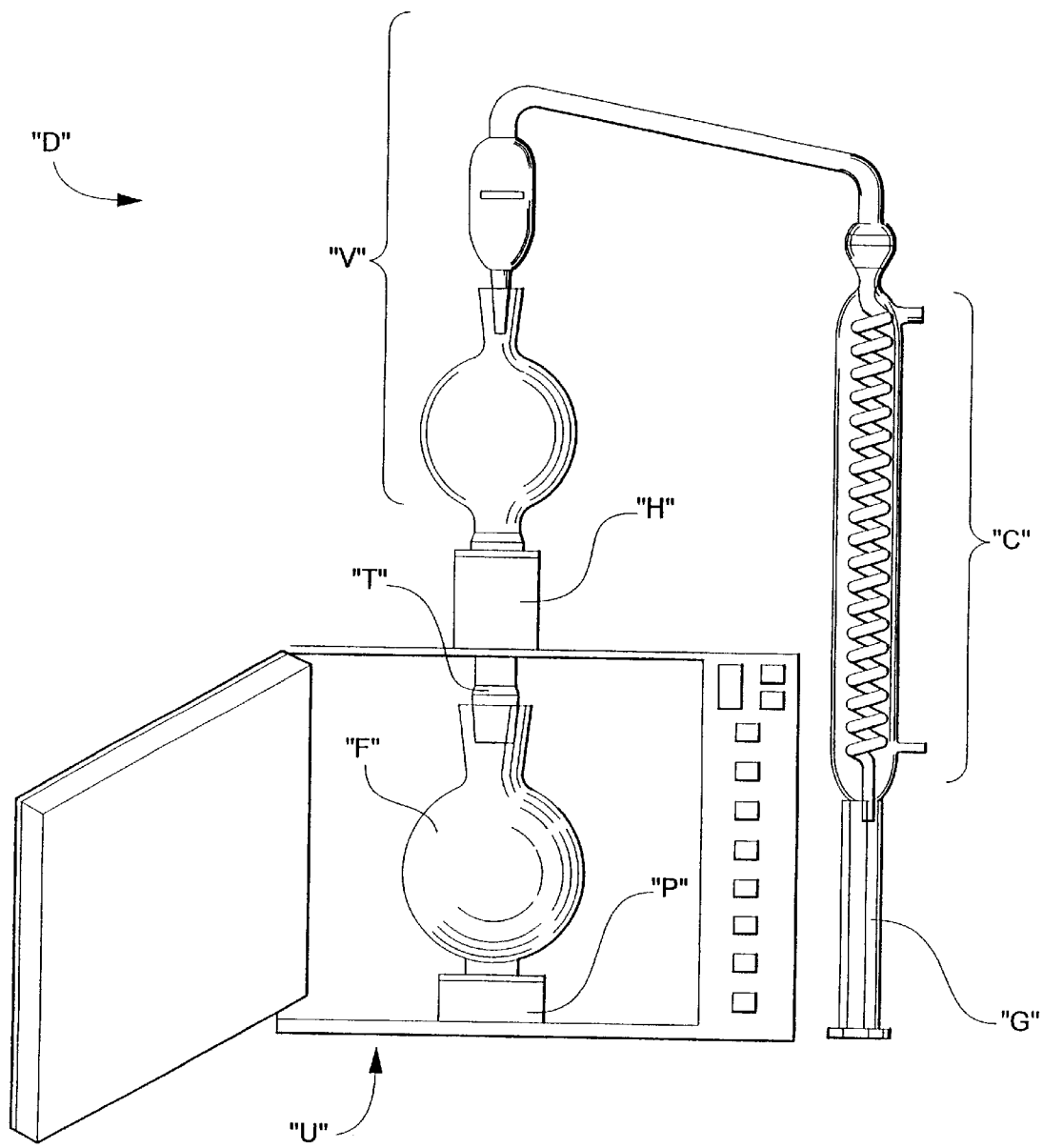
FIG. 1 is an elevational view of a prior art microwave distillation apparatus with an access door of the apparatus removed.
Figure 2:
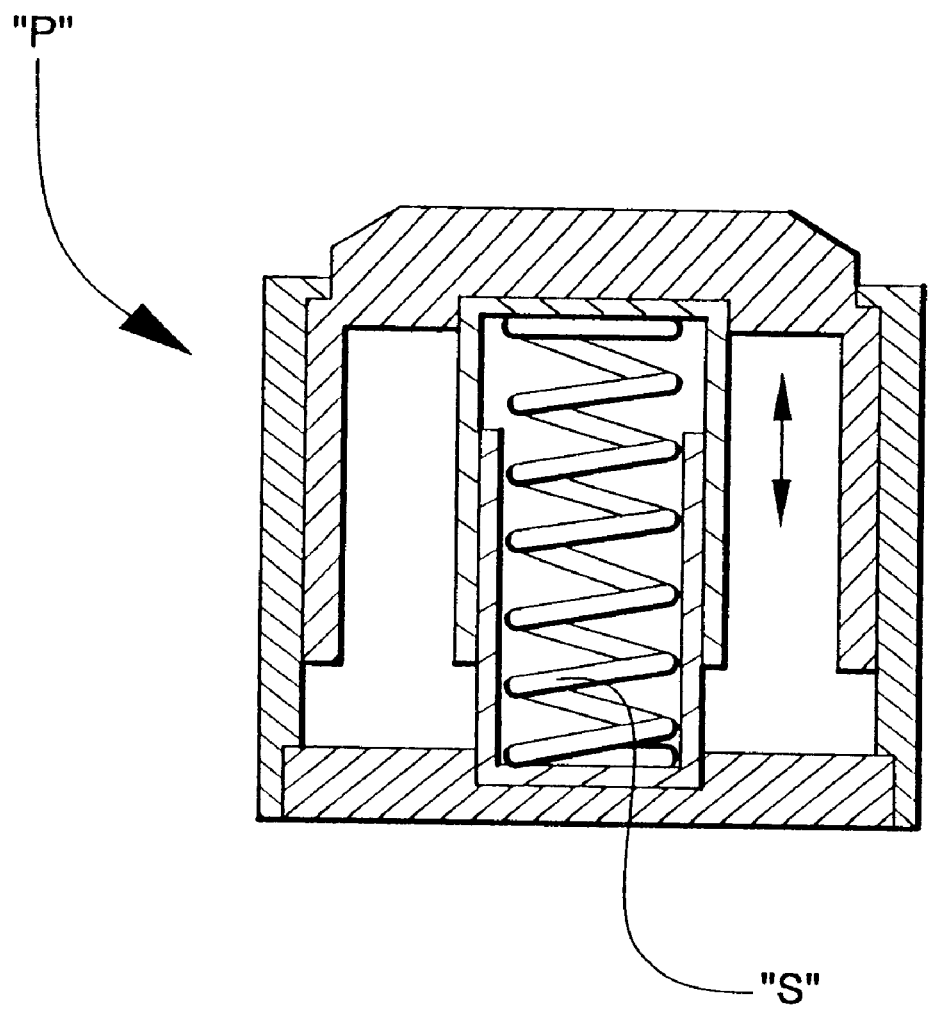
FIG. 2 is a cross-sectional view of a pedestal spacer with biasing means for being located within a microwave unit of the prior art distillation apparatus.
Figure 3:
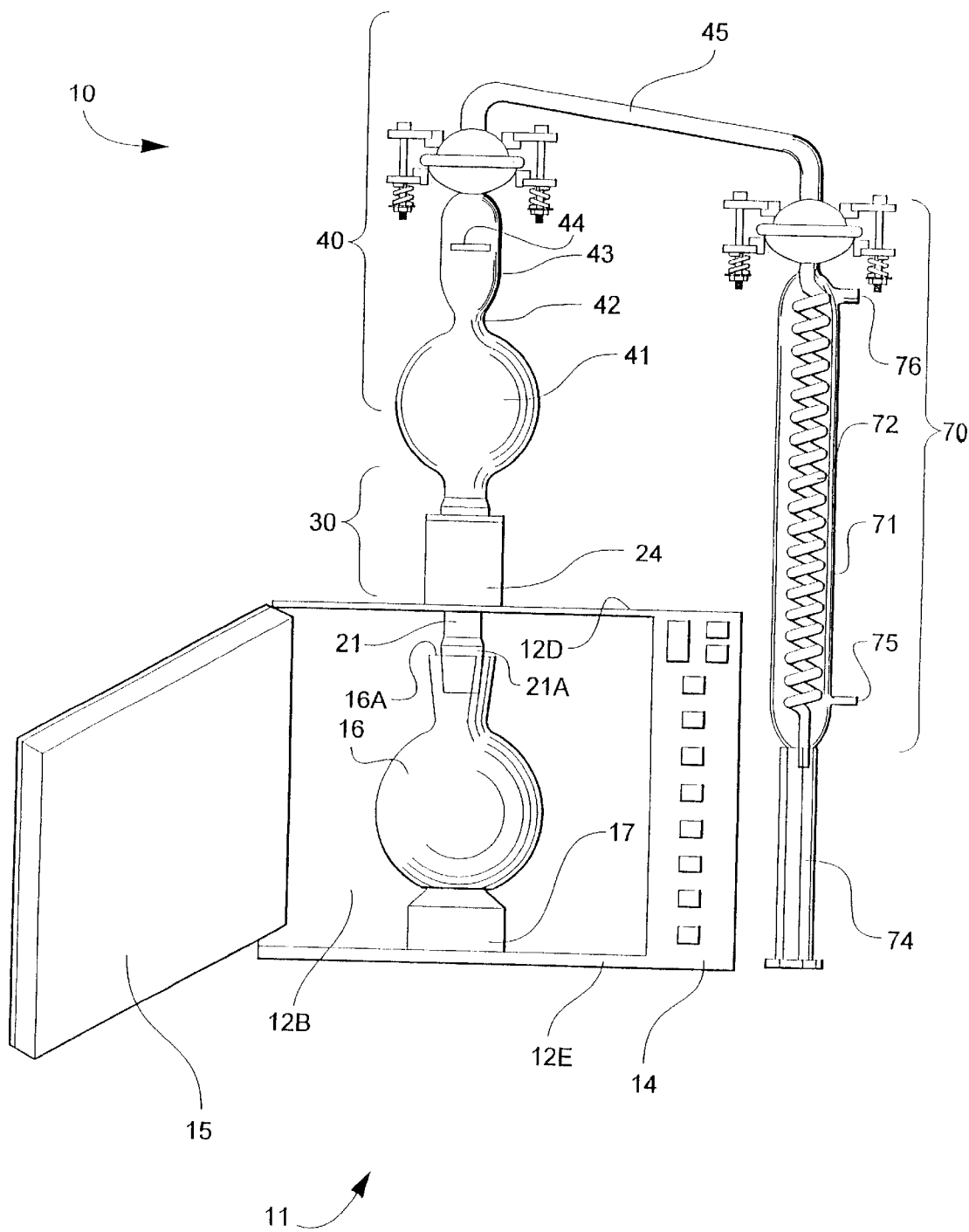
FIG. 3 is an elevational view of the present distillation apparatus with an access door of the microwave chamber opened to show the vessel inside the chamber.

Referring now specifically to the drawings, a microwave distillation apparatus according to the present invention is illustrated in FIG. 3 and shown generally at reference numeral 10. The distillation apparatus 10 is suitable for quick and efficient distillation of beverages, such as citrus juices, using microwave energy. A previously described prior art embodiment of a distillation apparatus is shown in FIGS. 1 and 2.

Figure 4:
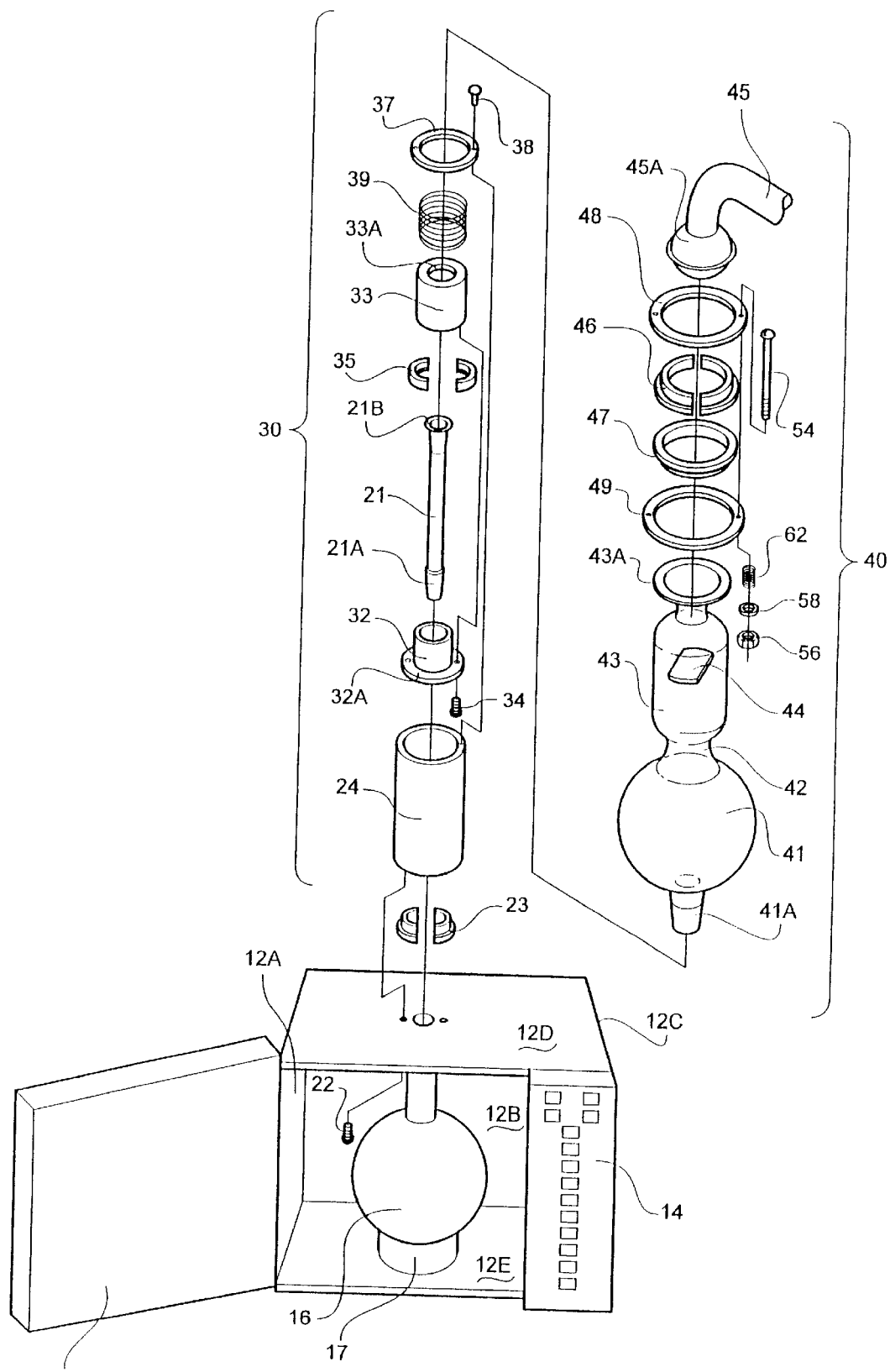
FIG. 4 is an exploded perspective view of the present microwave distillation apparatus according to one preferred embodiment of the invention.

Referring to FIGS. 3 and 4, the present distillation apparatus 10 utilizes a microwave heating chamber 11, such as a conventional microwave unit or microwave oven with ceramic floor, biasing assembly 30, and a vapor transfer assembly 40 and condenser assembly 70 for capturing the liquid distillate. Each of these elements are discussed separately below.

Microwave Heating Chamber 11

The heating chamber 11 includes attached side walls 12A, 12B, 12C, top and bottom walls 12D and 12E, a microprocessor control panel 14, and an access door 15. A vessel 16 is located within the heating chamber 11, and is supported above the bottom wall 12E of the chamber 11 by a microwave transparent pedestal spacer 17. Preferably, the vessel 16 is a standard glass flask, and includes a mouth 16A for receiving the sample to be distilled.

A glass connecting tube 21 extends through an opening in the top wall 12D of the heating chamber 11, and into sealing engagement with the mouth 16A of the vessel 16. Preferably, the vessel-engaging end 21A of the connecting tube 21 and the mouth 16A of the vessel 16 define respective complementary tapered ground glass joints. An opposite end 21B of the connecting tube 21 extends outwardly from the heating chamber 11, and cooperates with the biasing assembly 30 to maintain the seal between the connecting tube 21 and vessel 16 during the distillation process.

Biasing Assembly 30

Figure 5:
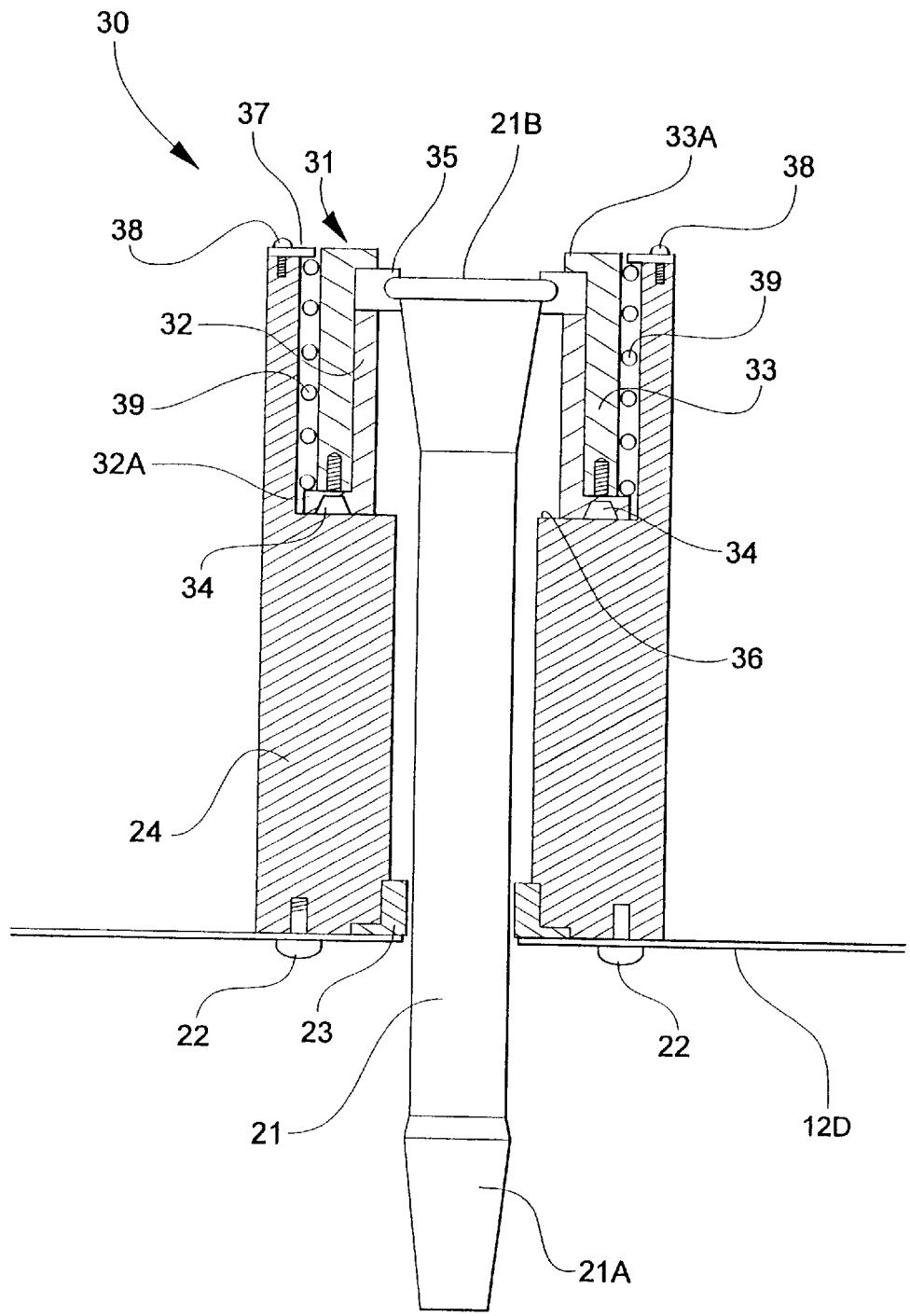
FIG. 5 is a fragmentary partial cross-sectional view of the housing mounted on a top wall of the microwave chamber of the present distillation apparatus, and showing the cylinder assembly and biasing spring.

Referring to FIGS. 3, 4, and 5, the biasing assembly 30 according to the embodiment disclosed includes a cylindrical metal housing 24 mounted outside of the heating chamber 11, and surrounding the end 21B of the connecting tube 21. The metal housing 24 is preferably attached to the top wall 12D of the heating chamber 11 with one or more screws 22, and is not exposed to microwave energy. A split teflon ring 23 is located at a bottom opening of the housing 24 for protecting the glass surface of the connecting tube 21 against damage as the vessel 16 is inserted into and removed from the heating chamber 11.

As best shown in FIG. 5, the housing 24 contains a cylinder assembly 31 secured to the connecting tube 21, and positioned for biasing movement within the interior of the housing 24. The cylinder assembly 31 is preferably formed of nested inner and outer cylinders 32 and 33 held together by one or more flat head screws 34. The inner cylinder 32 includes an outwardly turned bottom flange 32A. The outer cylinder 33 is mounted on the bottom flange 32A of the inner cylinder 32, and includes an inwardly-turned top flange 33A. An annular split teflon ring 35 is located between the top flange 33A of the outer cylinder 33 and an annular top surface of the inner cylinder 32 for engaging and securely holding the end 21B of the connecting tube 21 within the cylinder assembly 31.

The bottom flange 32A of the inner cylinder 32 contacts an inside shoulder 36 formed in the housing 24, and restricts movement of the cylinder assembly 31 in a downwardly direction towards the vessel 16. An inwardly-extending annular top ring 37 is secured by one or more screws 38 to a top end of the housing 24, and restricts movement of the cylinder assembly 31 upwardly away from the vessel 16.

A resilient metal coil spring 39 is located between and engages the inwardly-extending top ring 37 of the housing 24 and the outwardly-extending bottom flange 32A of the inner cylinder 32. The spring 39 normally urges the cylinder assembly 31 downwardly against the inside shoulder 36 of the housing 24, and cooperates with the pedestal spacer 17 to maintain the seal between the connecting tube 21 and the mouth 16A of the vessel 16 as the liquid sample is heated in the chamber 11. The resulting vapors move outwardly from the vessel 16, through the connecting tube 21, and into the vapor transfer assembly 40, as discussed below.

Vapor Transfer Assembly 40

A surge bulb 41 is removably connected to the end 21B of the connecting tube 21 for receiving sudden spurts of liquid and vapors from the vessel 16 as the liquid is heated to a boil in the heating chamber 11. Preferably, the surge bulb 41 has an external ground glass joint 41A for sealably mating with an internal ground glass joint formed at the end 21B of the connecting tube 21.

A neck 42 of reduced diameter is formed adjacent to the surge bulb 41 opposite its external joint 41A, and serves to limit the sudden spurting of heated liquid outwardly from the surge bulb 41. Preferably, the diameter of the neck 42 is about one-fifth the center diameter of the surge bulb 41. A deflector cylinder 43 is formed with the neck 42, and includes a deflector plate 44 to block further outward spurting of heated liquid. The deflector plate 44 is generally rectangular shaped to define respective side openings between the wall of the deflector cylinder 43 and opposite side edges of the deflector plate 44, thereby permitting free movement of vapors upwardly through the deflector cylinder 43.

Preferably, the surge bulb 41, neck 42, and deflector cylinder 43 define a single integral unit which is mounted in substantial linear registration with the connecting tube 21 and vessel 16. As a result, when the vessel 16 is placed within the heating chamber 11, the biasing assembly 30 imparts a biasing linear force on the engaging elements which acts to effectively maintain the seal between the respective connections during distillation.

Figure 6:
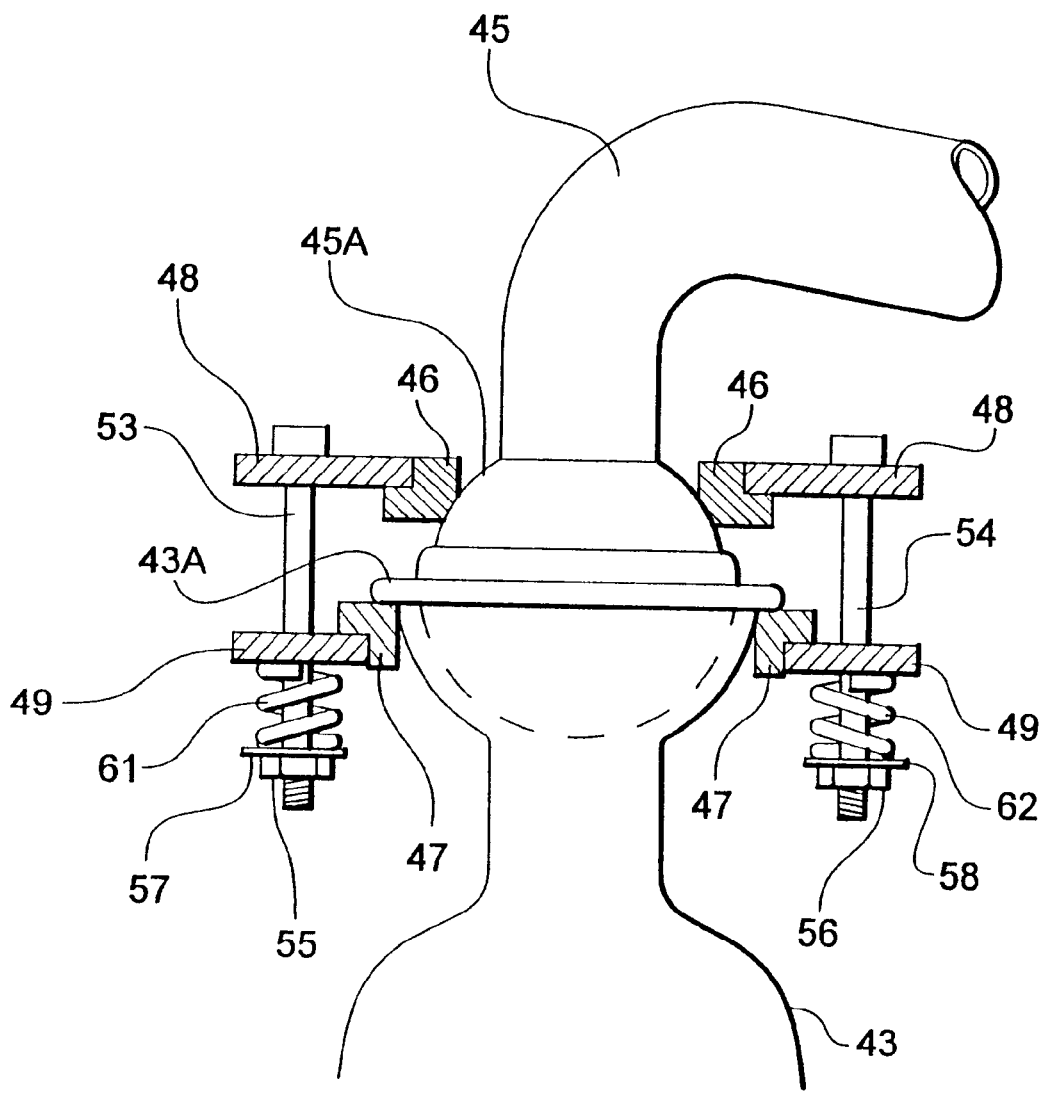
FIG. 6 is a fragmentary partial cross-sectional view of a clamping assembly for sealably connecting elements of the present distillation apparatus.

Referring to FIGS. 4 and 6, a glass vapor tube 45 sealably engages the deflector cylinder 43 for receiving vapors emitted from the heated liquid of the vessel 16. Preferably, the contacting portions of the deflector cylinder 43 and vapor tube 45 define a complementary ground glass spherical joint 43A and ball joint 45A, respectively.

A pair of split teflon rings 46 and 47 and annular top and bottom clamping plates 48 and 49 cooperate to maintain the seal between the vapor tube 45 and deflector cylinder 43. The clamping plates 48 and 49 are preferably held together by threaded bolts 53 and 54 extending through each of the plates 48 and 49, and complementary threaded nuts 55 and 56. Washers 57 and 58 and springs 61 and 62 are located respectively between the bottom plate 49 and the nuts 55 and 56. The springs 61 and 62 and teflon rings 46 and 47 permit slight movement of the clamping plates 48 and 49 to allow adjustment for thermal variations while maintaining a leakproof seal.

The vapors of the heated liquid pass through the vapor transfer assembly 40, as described above, and into the condenser assembly 70.

Condenser Assembly 70

Figure 7:
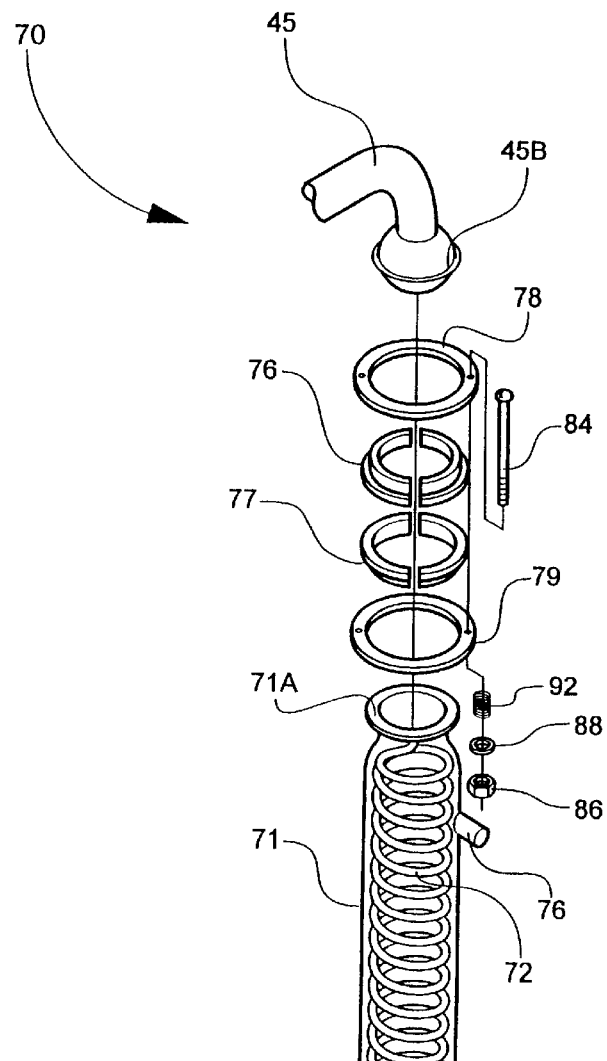
FIG. 7 is an exploded perspective view of the condenser assembly of the present distillation apparatus.
Figure 8:
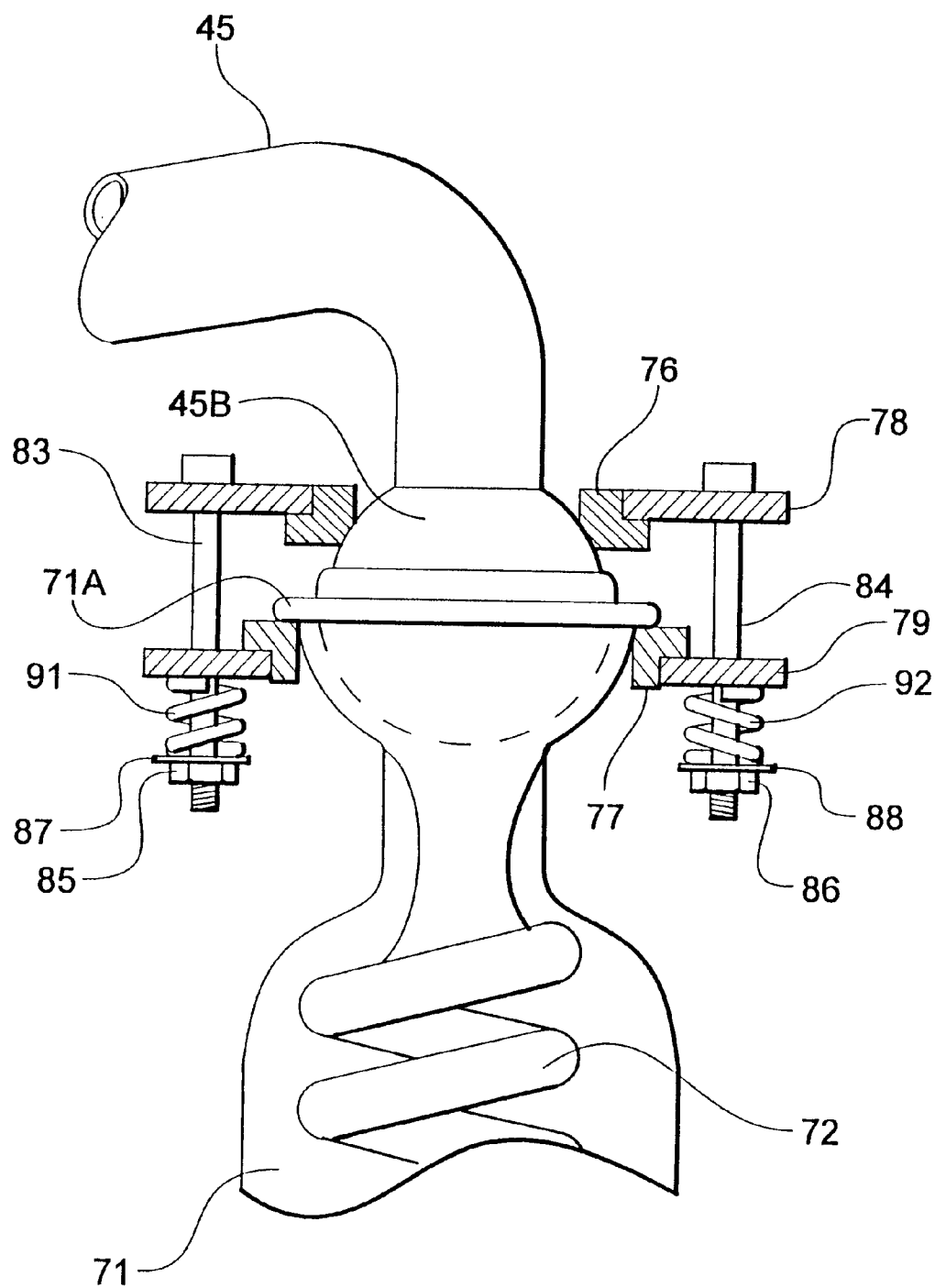
FIG. 8 is a fragmentary partial cross-sectional view of a clamping assembly like that shown in FIG. 6 for sealably connecting elements of the present distillation apparatus.

Referring to FIGS. 3, 7, and 8, the condenser assembly 70 includes an outer glass jacket 71, and condenser coil 72 contained within the jacket 71 for receiving the vapors from the vapor transfer assembly 40. Preferably, the end 45B of the vapor tube 45 is sealably connected to a mouth 71A of the outer glass jacket 71 in an identical manner as described above with regard to the connection between the vapor tube 45 and deflector cylinder 43. Vapors entering the mouth 71A of the outer glass jacket 71 pass directly into the condenser coil 72.

As best shown in FIG. 8, a pair of split teflon rings 76 and 77 and annular top and bottom clamping plates 78 and 79 cooperate to maintain the seal between the vapor tube 45 and mouth 71A of the outer glass jacket 71. The clamping plates 78 and 79 are preferably held together by threaded bolts 83 and 84 extending through each of the plates 78 and 79, and complementary threaded nuts 85 and 86. Washers 87 and 88 and springs 91 and 92 are located respectively between the bottom plate 79 and the nuts 85 and 86. The springs 91 and 92 and teflon rings 76 and 77 permit slight movement of the clamping plates 78 and 79 to allow adjustment for thermal variations while maintaining a leak-proof seal.

The condenser coil 72 receives and cools the vapors, and ultimately transforms the vapors into a liquid state. The resulting distillate passes outwardly from the jacket 71 and condenser coil 72, and is captured in a collection vessel 74 for testing.

The glass jacket 71 further includes an inlet 75 for receiving a cooling fluid into a bottom end of the glass jacket 71, and an outlet 76 for discharging the fluid at a top end of the jacket 71 as the fluid is warmed by the vapors in the condenser coil 72. Thus, a cooling fluid is continually recycled through the jacket 71 as the vapors change into the liquid distillate.

Operation of the Distillation Apparatus 10

To initiate the distillation process, the user properly positions the vessel 16 and pedestal spacer 17 within the microwave chamber 11, and creates the seal between the connecting tube 21 and mouth 16A of the vessel 16. The resiliency of the spring 37 of the biasing assembly 30 allows slight adjustment of the connecting tube 21 as it is received into the vessel 16. Preferably, silicone grease or other suitable lubricant is applied to the connecting tube 21 and mouth 16A of the vessel 16 to enhance the seal. The access door 15 of the chamber 11 is then closed, and the microwave control panel 14 set for 4–5 minutes.

As the liquid sample is heated to boiling, vapors and spurts of liquid pass outwardly from the vessel 16, through the connecting tube 21, and into the surge bulb 41. The interior of the microwave chamber 11 includes only microwave transparent elements during heating to maximize the efficiency of microwave energy, and thereby decrease the boiling time of the sample. The biasing assembly 30 located outside of the chamber 11 serves to maintain the seal between the vessel 16 and connecting tube 21 as the liquid is heated.

The neck 42, deflector cylinder 43, and deflector plate 44 act to block any sudden spurts of heated liquid outwardly from the surge bulb 41, while permitting free passage of vapors into and through the vapor transfer tube 45. The vapors pass from the vapor tube 45 into the condenser coil 72 where the vapors are cooled and transformed into a liquid state. The resulting liquid distillate is captured in the collection vessel 74 for testing.

Preferably, each of the elements of the distillation apparatus 10 for containing the liquid sample, vapors, and distillate are made of glass. In addition, the biasing assembly 30 described above is usable in other applications for maintaining a seal between the mouth of a vessel and a connecting tube, or other removable top or closure.

A microwave distillation apparatus is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. In combination with a vessel for being located within a microwave heating chamber, and having an open mouth for receiving a liquid, said combination comprising:

(a) a hollow connecting tube for extending through a wall of the heating chamber and having opposing first and second ends, the first end of said connecting tube defining an annular opening located outside of the heating chamber and the second end of said connecting tube being arranged in sealing engagement with the mouth of the vessel;

(b) a housing mounted outside of the heating chamber and surrounding the first end of said connecting tube, said housing including an inwardly-extending top flange and an inside shoulder vertically spaced apart from the top flange;

(c) a cylinder assembly movable within said housing and including a top ring and an outwardly-extending bottom flange, the top ring engaging an entire circumference of the annular opening formed at the first end of said connecting tube, and the bottom flange of the cylinder assembly contacting the inside shoulder of the housing to restrict movement of the cylinder assembly within said housing in a direction towards said vessel; and (d) a coil spring located between and engaging the inwardly-extending top flange of the housing and the outwardly-extending bottom flange of the cylinder assembly, said spring normally urging the bottom flange of said cylinder assembly against the inside shoulder of the housing to thereby maintain the seal between the second end of said connecting tube and the mouth of the vessel.

2. A biasing assembly for use in combination with a vessel for being located within a microwave heating chamber, the vessel having an open mouth for receiving a liquid, and a connecting tube for extending through a wall of the heating chamber and having opposing first and second ends, the first end of the connecting tube defining an annular opening located outside of the heating chamber and the second end of the connecting tube being arranged in sealing engagement with the mouth of the vessel; said biasing assembly comprising:

(a) a housing for being mounted outside of the heating chamber and adapted for surrounding the first end of the connecting tube, said housing including an inwardly-extending top flange and an inside shoulder vertically spaced apart from the top flange;

(b) a cylinder assembly movable within said housing, and including a top ring and an outwardly-extending bottom flange, the top ring being adapted for engaging an entire circumference of the annular opening formed at the first end of the connecting tube, and the bottom flange of the cylinder assembly contacting the inside shoulder of the housing to restrict movement of the cylinder assembly within said housing in a direction towards the vessel; and (c) a coil spring located between and engaging the inwardly-extending top flange of the housing and the outwardly-extending bottom flange of the cylinder assembly, said spring normally urging the bottom flange of said cylinder assembly against the inside shoulder of the housing to thereby maintain the seal between the second end of said connecting tube and the mouth of the vessel.

* * * * *